(12) United States Patent
Blacklock

(10) Patent No.: US 6,679,701 B1
(45) Date of Patent: Jan. 20, 2004

(54) ANCHOR HAVING THREADS OPPOSING UNTHREADING

(76) Inventor: Gordon D. Blacklock, 14116 Grand NE., Albuquerque, NM (US) 87123

(*) Notice: Subject to any disclaimer, the term of this patent is extended or adjusted under 35 U.S.C. 154(b) by 0 days.

(21) Appl. No.: 09/533,256

(22) Filed: Mar. 23, 2000

(51) Int. Cl.$^7$ .................................................. A61C 8/00
(52) U.S. Cl. .......................................................... 433/174
(58) Field of Search ...................................... 433/173, 174

(56) References Cited

U.S. PATENT DOCUMENTS

| | | | |
|---|---|---|---|
| 4,826,434 A | 5/1989 | Krueger | |
| 4,863,383 A | 9/1989 | Grafelmann | |
| 4,932,868 A | 6/1990 | Linkow et al. | |
| 5,088,926 A | * 2/1992 | Lang | 433/173 |
| 5,269,685 A | * 12/1993 | Jorneus | 433/174 |
| 5,312,256 A | 5/1994 | Scortecci | |
| 5,324,199 A | * 6/1994 | Branemark | 433/174 |
| 5,427,527 A | 6/1995 | Niznick et al. | |
| 5,437,551 A | 8/1995 | Chalifoux | |
| 5,601,429 A | 2/1997 | Blacklock | |
| 5,816,812 A | * 10/1998 | Kownacki et al. | 433/174 |
| 5,915,967 A | 6/1999 | Clokie | |
| 6,099,312 A | * 8/2000 | Alvaro | 433/174 |
| 6,135,772 A | * 10/2000 | Jones | 433/174 |

OTHER PUBLICATIONS

"Why The World Is Attached To Osseotite . . . ", sales brochure of Implant Innovations, Inc., of Palm Beach Gardens, FL 33410, dated 1998.

\* cited by examiner

*Primary Examiner*—Nicholas D. Lucchesi
(74) *Attorney, Agent, or Firm*—Siemens Patent Services, LC

(57) ABSTRACT

A threaded implement, such as a dental or medical implant having a receptacle bearing a socket for receiving or securing a threaded shank for engaging material such as bone tissue, the threads bearing longitudinally oriented grooves for opposing spontaneous unthreading over time. Alternatively, the implement could be a general purpose anchor or an industrial fastener wherein resisting unthreading is important. The grooves extend from the lower end of the implant toward the upper portion. In a first embodiment, the grooves are shallow, and in another embodiment, are deep enough to impinge upon the shank. Each groove has a first face disposed perpendicularly or nearly so to the circumferential surface when viewed in side cross section and a second face disposed more closely to parallel to the circumferential surface when viewed in side cross section. The first face is oriented such that it faces away from the direction of advance when the implant is threaded into the bone. In a second embodiment, the grooves are replaced by outward projections which displace bone axially when the implant is being threaded into bone tissue. In other alternative embodiments, the grooves may abut one another, may be spaced apart along the circumferential surface, and may include a third face separating the first and second faces. In further alternative embodiments, the shank is tapered, the receptacle is cylindrical, and the receptacle has a non-cylindrical, plain walled cylindrical, or internally threaded cylindrical recess opening at the upper end of the receptacle.

30 Claims, 5 Drawing Sheets

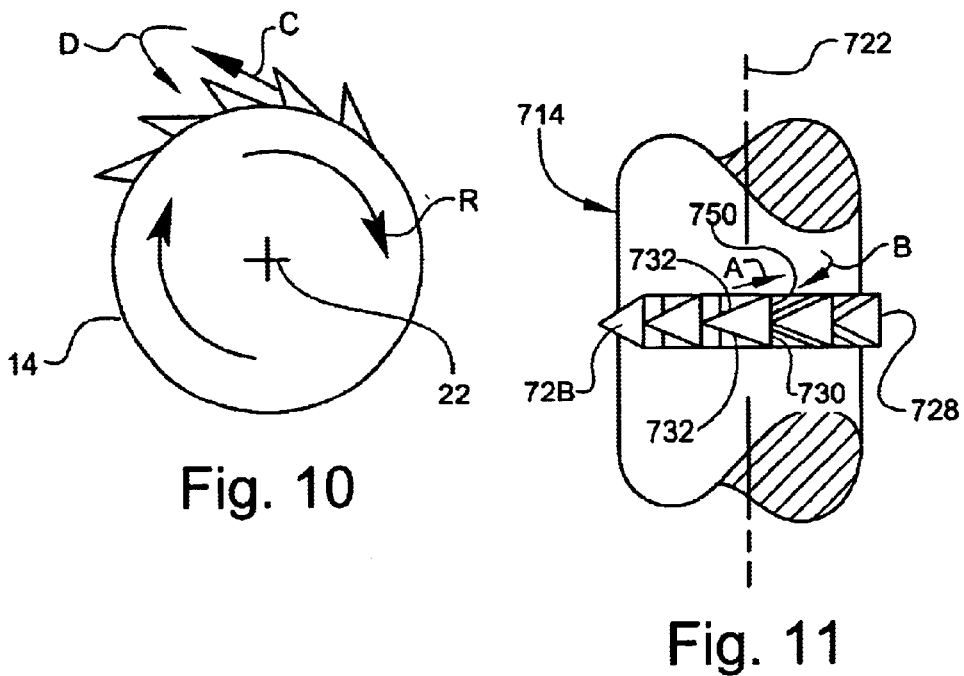
Fig. 10
Fig. 11
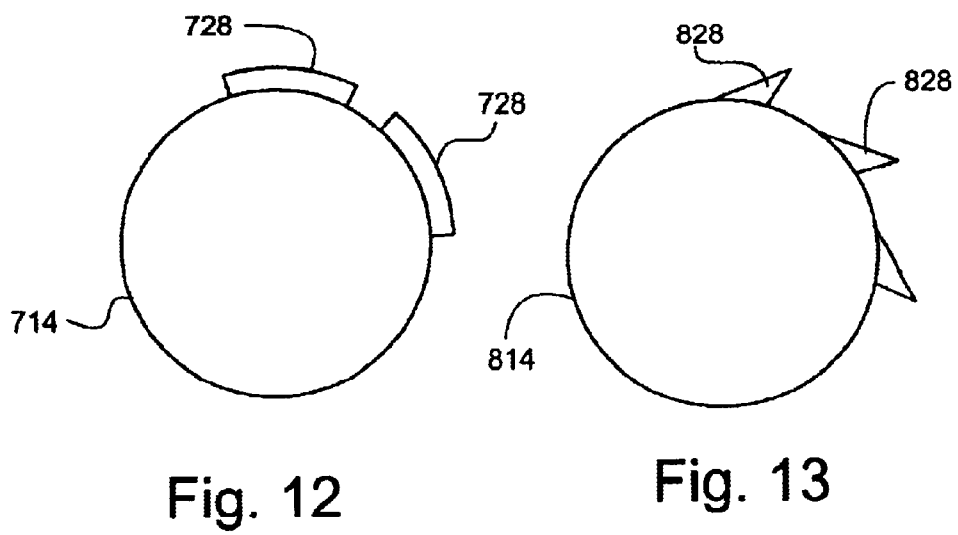
Fig. 12
Fig. 13

ANCHOR HAVING THREADS OPPOSING UNTHREADING

BACKGROUND OF THE INVENTION

1. Field of the Invention

The present invention relates to anchors for supporting an object on a supporting substrate. A specific example of such anchors includes the field of dental implants of the type permanently installed into a patient's bone, such as a jaw bone. More particularly, the invention improves retention of an anchor by configuring grooves or channels cut into external threads of the anchor such that spontaneous counter-rotation or unthreading of the anchor is opposed. The invention is also usable in the form of industrial fasteners. The invention finds utility wherever anchors are threaded into a solid supporting object for long term installation. It is contemplated that the primary applications will be those of dental and other medical anchors or implants, and associated prostheses.

2. Description of the Prior Art

In the field of dental prostheses, a trend has developed favoring anchoring of prostheses in the jaw bones of patients. Particularly as biocompatible materials have become available, it is possible to contemplate long term successful installations of prostheses. The process of implantation begins with placement of the anchoring element, or implant, within the jaw. Most implants are threaded into a hole bored into the jaw, or are pressed into a similar hole. After the implant has become osseointegrated, the prosthesis, mounted on a suitable post, is fixed to the implant in a subsequent step.

It will be appreciated that natural teeth and prostheses functioning in a similar manner are subjected to great forces, such as repeated compression and recovery cycles. It is possible for the implant to unthread spontaneously and become loose. Implants are quite small, and can be swallowed or otherwise lost. Even if they are retained, looseness can cause injury and subsequent loss if chewing and biting are attempted.

The prior art has recognized the problem of unintended detachment of the implant. U.S. Pat. No. 4,826,434, issued to Kenneth K. Krueger on May 2, 1989, shows a dental implant having axial grooves cut through threads at the distal end of the implant. Each of these grooves has a first face arranged perpendicularly or nearly so to the outer circumferential surface of the implant, and a second face oriented at an angle such that the second face is closer to parallel to the circumferential surface than is the first face.

However, in Krueger, the grooves are oriented in a manner typical of self-tapping screws, that is, the perpendicular face is exposed in the direction of motion during threading. By contrast, this orientation is reversed in the present invention. While any irregularity formed in threads will oppose unthreading due to increased surface area of osteointegration, the orientation of the present invention acts more in ratchet fashion, thereby more effectively opposing unthreading.

Also, in Krueger, these grooves are located at the distal end of the implant. By contrast, corresponding grooves in the present invention extend for longer along the length of the threaded section of the implant. In Krueger, the grooves are quite short, and cut entirely through the threads and extend into the shank.

U.S. Pat. No. 4,932,868, issued to Leonard I. Linkow et al. on Jun. 12, 1990, illustrates an implant having axially oriented grooves cut through the threads. Each groove has one face arranged nearly perpendicularly to the outer circumferential surface of the implant, and a second face oriented at an angle much closer to parallel to the outer circumferential surface. By contrast with Linkow et al., the present invention reverses the relative positions of the two faces of each groove. The novel arrangement forgoes bone shaving asserted to occur by Linkow et al., but gains instead ability to resist spontaneous counter-rotation or unthreading of the implant.

U.S. Pat. No. 4,863,383, issued to Hans L. Grafelmann on Sep. 5, 1989, illustrates a dental implant having axially oriented grooves for self-tapping purposes. The grooves are similar to those of the device of Linkow et al., and share structural dissimilarities distinguishing the present invention from those of Krueger, Linkow et al. and Grafelmann.

My prior U.S. Pat. No. 5,601,429, issued on Feb. 11, 1997, describes a dental implant having relief grooves formed transversely in exterior threads. The threads have surface pitches disposed to oppose unthreading. However, the grooves of the prior issued patent do not have characteristics of the present invention.

None of the above inventions and patents, taken either singly or in combination, is seen to describe the instant invention as claimed.

SUMMARY OF THE INVENTION

The present invention provides an anchor which has structure opposing spontaneous withdrawal or loosening. As described herein, the invention will be described in terms of a threaded dental implant, it being understood that the inventive concept is equally applicable to other anchors and fasteners wherein it is desired to oppose unthreading. The threads of the implant are interrupted by axially or longitudinally oriented grooves or channels. Each groove has a first face oriented perpendicularly or nearly so to the circumferential outer surface of the implant, and a second face which assumes an orientation much closer to parallel to the circumferential surface than is the first face.

The first face is located so that it does not oppose threading of the implant into its associated hole. However, because of resiliency of bone tissue, reversal of the direction of rotation in which the implant is installed will cause interference as the retentive element snags bone tissue. Therefore, the second face acts in the manner of a ratchet allowing one direction of rotation yet opposing the opposite direction.

The grooves are formed above the distal end of the implant, where the distal end is that first contacting the hole and bone tissue when the implant is installed. The grooves extend along a tapered or generally frustoconical section of the implant almost to the socket portion, where the socket portion is that portion which is cylindrical at its outer surface and which bears structure for engaging the post of the prosthesis. The grooves therefore extend along the implant for a significant distance of the threaded portion thereof. The undisturbed threads serve as starting threads. In some embodiments, the grooves do not cut entirely through the threads and therefore do not intrude upon the frustoconical shank bearing the threads. In other embodiments, the threads are sufficiently deep to intrude upon the shank.

In the first embodiment, bone tissue is displaced radially both when being compressed and when expanding. In an alternative embodiment of the invention, the grooves are replaced by projections generally configured as arrowheads having leading and trailing faces arranged to displace bone tissue axially with respect to the implant. As each projection passes, bone tissue expands resiliently in an axial direction opposite to that in which it was compressed. The trailing face in the second embodiment is arranged perpendicularly or nearly so to the axis of rotation of the implant, whereas the leading face is arranged at a much less severe angle. The second embodiment therefore opposes rotation in a manner similar to that of the first embodiment, the difference being direction of displacement of bone tissue.

The improvement provides more immediate retention of an implant in bone tissue. The constituent material is biocompatible, titanium for example, and therefore contributes to the osteointegration process.

Implants of different configurations can enjoy the benefits of the invention. The socket may bear threaded and unthreaded cylindrical recesses for receiving the post of a prosthesis. The threaded shank may be tapered or cylindrical, and may be equal in diameter to the socket or alternatively may be smaller than the socket.

Accordingly, it is one object of the invention to provide an anchor which resists spontaneous unthreading from its anchorage in bone tissue.

It is another object of the invention to promote long service life of implanted dental and other prostheses supported in a live body by osteointegration.

It is a further object of the invention that the invention be applied to anchors having sockets and threaded shanks of different dimensions and configurations.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 10 is a diagrammatic top plan detail view of the embodiment of FIG. 1.

FIG. 11 is a diagrammatic side elevational view of another embodiment of the invention.

FIG. 12 is a diagrammatic, top plan detail view of one variation on the embodiment of FIG. 11.

FIG. 13 is a diagrammatic, top plan detail view of another variation on the embodiment of FIG. 11.

DETAILED DESCRIPTION OF THE PREFERRED EMBODIMENTS

Figure 1:
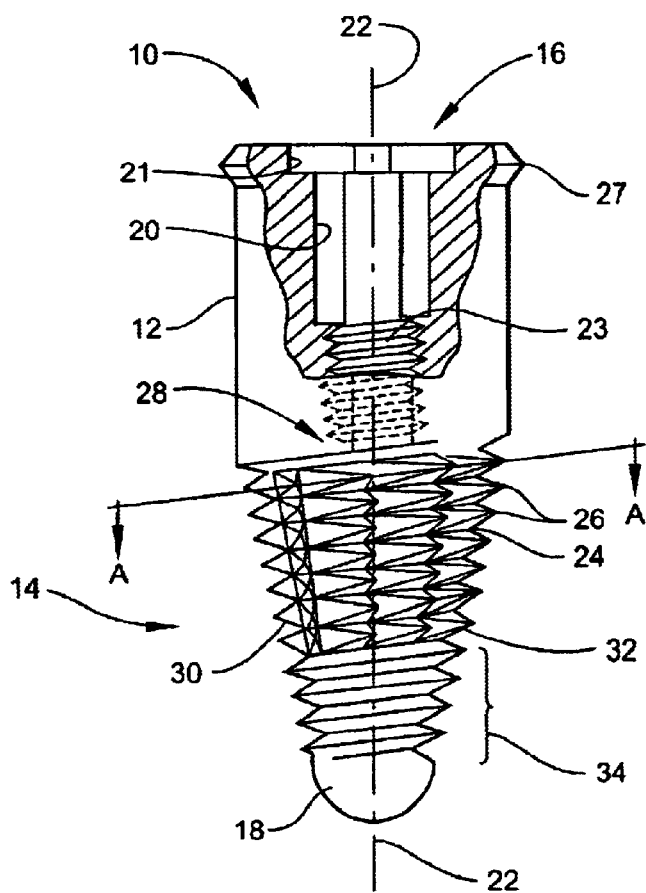
FIG. 1 is a side elevational view of one embodiment of the invention, shown partially in cross section.

FIG. 1 of the drawings shows a dental implant 10 for securing a prosthesis (not shown) within live bone tissue (not shown). Implant 10 comprises receptacle 12 having a socket for engaging the prosthesis and a shank 14 for anchoring receptacle 12 to the bone tissue. Implant 10 includes a proximal end 16 located at the upper end of receptacle 12 and a distal end 18 located at the lower end of shank 14. Distal end is domed or otherwise tapered. This characteristic imparts self-centering ability, thereby assuring the implant 10 will be true and properly installed within the jaw.

Receptacle 12 is integrally formed with or securely attached to shank 14, and has structure disposed to cooperate with and attach to the prosthesis. In the embodiment of FIG. 1, this structure is a hexagonal recess 20 which receives a hexagonal post (not shown) of the prosthesis in close cooperation.

This configuration is not critical, although the noncircular nature of recess 20 is preferred so that a tool (not shown) can be inserted into recess 20 and turned to thread implant 10 into a bore formed in bone tissue. Attachment of the prosthesis, which is performed after implant 10 is fully osseointegrated, is conventionally accomplished. Implant 10 is preferably fabricated from nearly pure titanium or any other physiochemically inert material which will survive in the environment of a live body.

Figure 2:
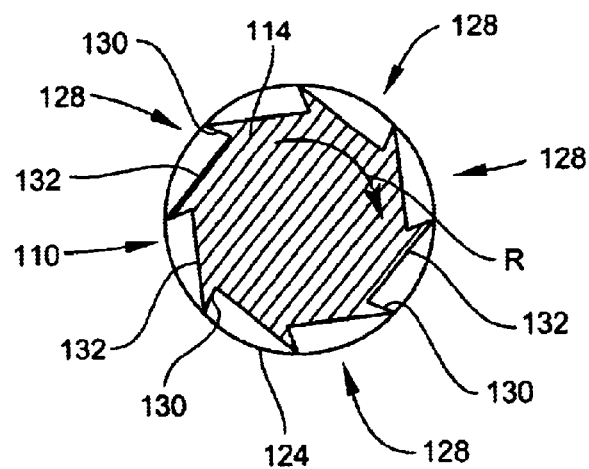
FIG. 2 is a diagrammatic top plan view of a second embodiment of the invention, and corresponds to the section of FIG. 1 indicated by line A—A.

Shank 14 has an elongate body including a longitudinal axis 22 which is preferably common to receptacle 12, an external circumferential surface 24, and threads 26. Threads 26 extend substantially along shank 14 outside external surface 24 other than parallel to axis 22. A groove 28 is formed to interrupt threads 26, and is oriented at a non-parallel angle thereto. Groove 28 is formed in threads 26 such that it has a first face 30 disposed at a relatively great angle to circumferential surface 24 and is exposed in a direction opposite to the direction of advance when dental implant 10 is threaded into the bone tissue. Groove 28 also has a second face 32 disposed at a relatively lesser angle to circumferential surface 24. Turning momentarily to FIG. 2, arrow R indicates direction of rotation when threading implant 110 into bone tissue. This direction applies for all right handed threads, which are depicted in all embodiments illustrated herein. It will be seen that faces 130 (and corresponding faces in the other embodiments) are exposed opposite to the direction of advance. Of course, the opposite would be true if the thread were left handed.

Groove 28 terminates at a point above distal end 18 of implant 10 such that an area 34 unencumbered by groove 28 exists on shank 14 between distal end 16 of implant 10 and groove 28. Of course, groove 28 may extend entirely to the distal end 18 in some applications. Groove 28 is long enough to interrupt more than just the first few threads 26, and preferably each turn of threads 26. Therefore, groove 28 forms first and second faces 30, 32 in most turns of threads 26. Faces 30 and 32 are respectively vertically aligned in the depiction of FIG. 1, as would result from a single vertical pass of a machining, abrading, or comparable tool (not shown) across threads 26.

FIG. 2 shows another embodiment of the invention wherein plural, abutting grooves 128 are formed in shank 114 of an implant 110 which is otherwise similar to implant 10 of FIG. 1. In the embodiment of FIG. 2, grooves 128 abut in that a first face 130 of one groove 128 abuts a second face 132 of another groove 128. It will be understood that faces 130 are arranged at an angle of or approaching perpendicular or nearly so to the outer circular boundary 124 which does not literally exist due to abutment of grooves 128, but which corresponds to surface 24 of the embodiment of FIG. 1.

Figure 3:
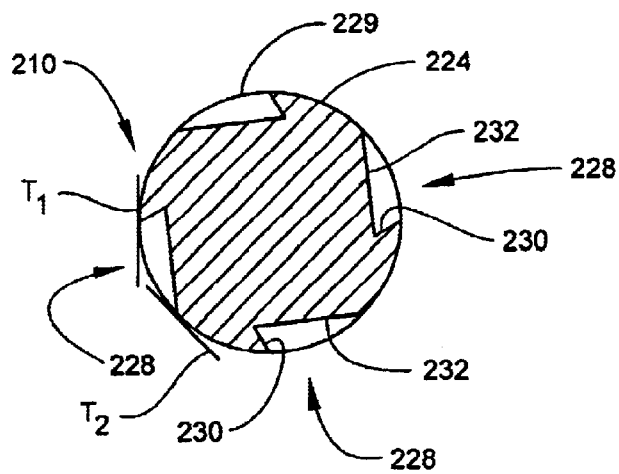
FIG. 3 is a diagrammatic top plan view of a third embodiment of the invention, and corresponds to the section of FIG. 1 indicated by line A—A.

In FIG. 3, implant 210 has grooves 228 which generally correspond to groove 28 of FIG. 1. Grooves 28 are spaced apart from one another such that said first faces 230 of grooves 282 are spaced out of abutment with second faces 232. Faces 230 of FIG. 3 correspond in orientation to faces 130 of FIG. 2 and face 30 of FIG. 1. Similarly, faces 232 of FIG. 3 correspond in orientation to faces 132 of FIG. 2 And face 32 of FIG. 1. Likewise, implant 210 has a circumferential surface 224 corresponding to circumferential surface 124 in FIG. 2. As can be seen in FIG. 3, first face 230 of groove 2B is oriented at a first angle relative to a first line T1 that is tangent to the circumferential surface 224 at the point of intersection of the first face 230 with the circumferential surface 224, the first face being exposed in a direction opposite to the direction of advance of the implant during implantation. The second face 232 is disposed at a second angle relative to a second line T2 that is tangent to the circumferential surface 224 at the point of intersection of the second face 232 with the circumferential surface 224. The seconds face is closer to being parallel with the second tangent line T2 than said first face 230 is to being parallel with first tangent line T1. This relative relationship of the first and second faces and the circumferential surface of the shank holds true for all of the grooves of all the embodiments of implant disclosed.

Figure 4:
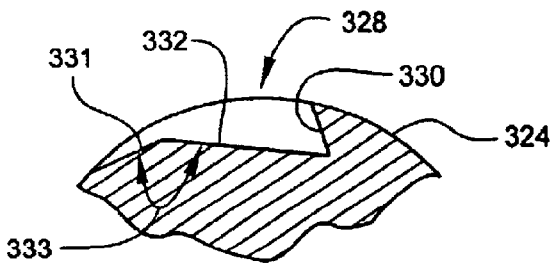
FIG. 4 is an enlarged detail view of a fourth embodiment of the invention.

FIG. 4 illustrates an embodiment of the invention wherein shank 314 has a groove 328, which is otherwise the equivalent of grooves 28, 128, and 228 of FIGS. 1, 2, and 3 (respectively), has a third face 331. Face 331 is disposed at a non-parallel angle 333 to face 332. It will be seen by examining FIG. 4 that face 331 is disposed at a non-parallel angle to face 330, although the angle which would otherwise be formed at the intersection of the planes of faces 330, 331 is not shown.

Figure 5:
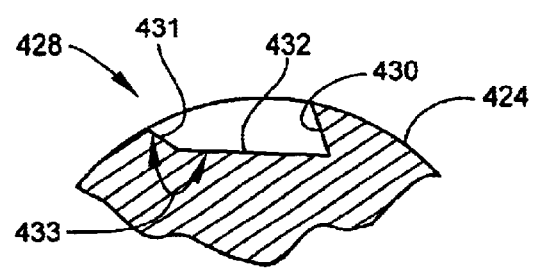
FIG. 5 is an enlarged detail view of a fifth embodiment of the invention.

FIG. 5 shows a variation on the embodiment of FIG. 4. In FIG. 5, a third face 435 is arranged at an angle 433 to face 432 such that groove 428 forms a trough having two lateral walls and a floor.

The various embodiments of grooves 28, 128, 228, 328, 428 shown and described herein may be applied to implants having structural differences compared to the embodiments of FIG. 1. In FIG. 1, receptacle 12 is cylindrical, and recess 20 is non-cylindrical, and more specifically, hexagonal. Configuration of receptacle 12 is a frequently employed configuration in the implant art, for cooperatively receiving a tool (not'shown) for turning the associated dental implant when threading it into the bone.

Figure 6:
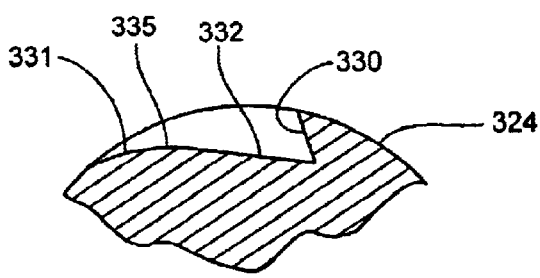
FIG. 6 is a top plan view of a sixth embodiment of the invention.
Figure 7:
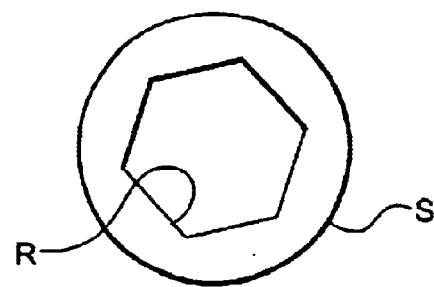
FIG. 7 is a top plan view of a seventh embodiment of the invention.

However, and referring now to FIG. 6, socket S of an implant (not shown in its entirety) formed according to the invention could comprise a cylindrical recess R formed therein and opening to the proximal end of the associated implant. In a further variation shown in FIG. 7, socket S could have two cylindrical recesses R.

Figures 8, 9:
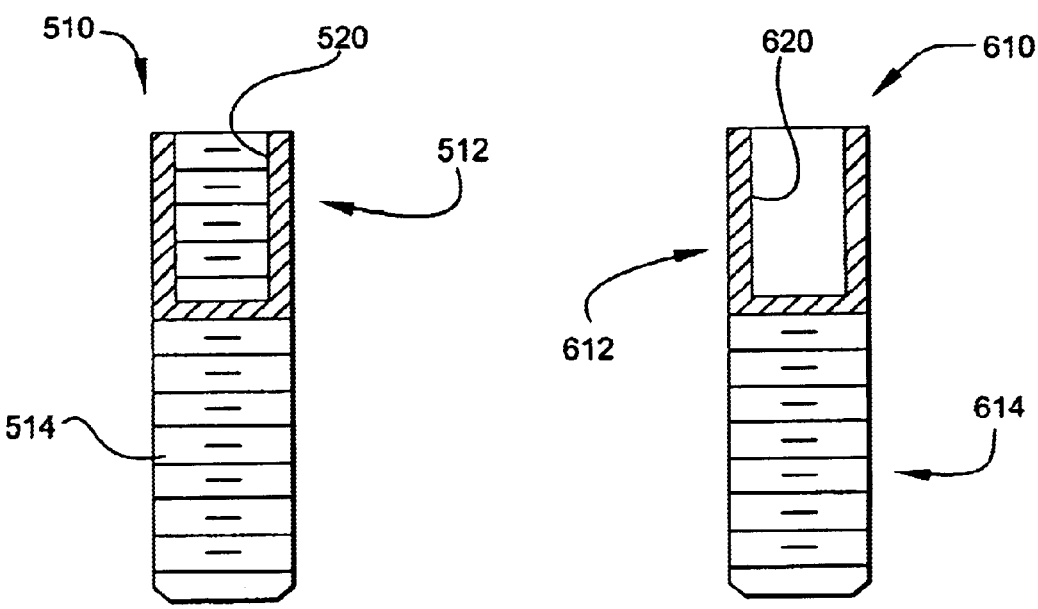
FIG. 8 is a side elevational view of an eighth embodiment of the invention, shown partially in cross section.
FIG. 9 is a side elevational view of a ninth embodiment of the invention, shown partially in cross section.

Noting that shank 14 of implant 10 is tapered, and more specifically is frustoconical, it is observed with reference to FIG. 8 that shank 514 of implant 510 is cylindrical and threaded. The threads of shank 514 have grooves corresponding to those of any one of the embodiments of FIGS. 1–6. Recess 520 is cylindrical and threaded.

There is no necessity that the threaded shank of an implant be of lesser diameter than that of the receptacle. As shown in FIG. 9, implant 610 has a receptacle 612 of diameter equal to that of threaded shank 614. Recess 620 has non-circular configuration, in this example being square. It will be understood that threading of shanks in all embodiments of the invention, where not explicitly described, will include grooves corresponding to any one of the embodiments of FIGS. 1–6.

The above embodiments share the characteristic that material supporting the threads, such as bone tissue in the example of implants, is displaced radially away from axis 22 when the implant is being threaded, the material expanding resiliently radially inwardly when the face arranged perpendicularly to the circumferential surface passes. It would be feasible to displace material in a direction parallel to axis 22 to the same effect. This is shown in FIG. 11, wherein a plurality of projections 728 are formed on shank 714 of another embodiment of the dental implant (not shown in its entirety) of the present invention. Each projection has leading faces 732 and a trailing face 730. As shank 714 is turned into material (not shown) and moves with the exposed side of shank 714 seen in FIG. 11 moving from right to left, bone is displaced as indicated by arrows A and B. Material is first displaced upwardly in a direction parallel to axis 722 of shank 714, as indicated by arrow A. Material is slightly compressed as it is displaced. As the material passes over the high point 750 of each projection 728, it resiliently expands downwardly, as indicated by arrow B, relieving compression to a certain degree.

This displacement may be contrasted with that of the embodiments of FIG. 1 by referring to FIG. 10. It must be recalled when making visual comparison that FIG. 10 is a top plan view, whereas FIG. 11 is a side elevational view. In FIG. 10, it is seen that material is first displaced radially away from axis 22, as indicated by arrow C. Material then resiliently expands inwardly, as indicated by arrow D. In the embodiment of FIG. 1, face 32 displaces material relative to shank 14. Face 30 engages material by direction interference so as to oppose rotation in a direction opposite the first direction. In the embodiment of FIG. 11, faces 732 displace material relative to shank 714, and face 730 is disposed in interference opposing counter-rotation in a manner similar to that of FIG. 1. A difference between FIGS. 1 and 11 is the direction of displacement of material. Opposition to counter-rotation is similar in manner in the two embodiments.

Figure 15:
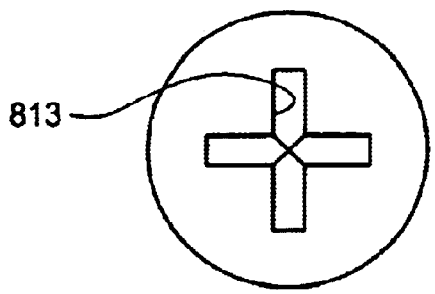
FIG. 15 is a top plan view of the embodiment of FIG. 14.
Figure 14:
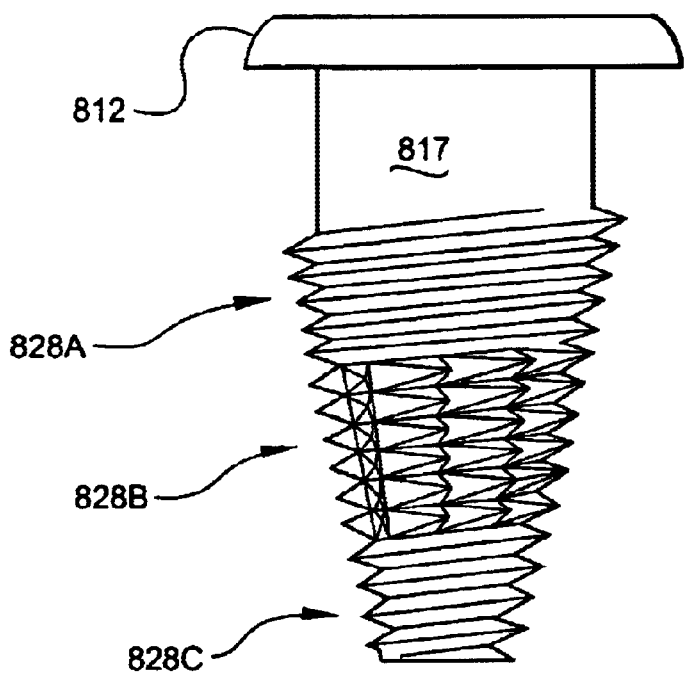
FIG. 14 is a side elevational view of an embodiment of the invention utilized as an industrial fastener.

FIG. 14 shows adaptation of the invention to the field of industrial fasteners. A screw 810 has a broad head 812 in the place of the receptacles of priorly described embodiments. Head 812 is configured to engage a driving tool. Illustratively, head 812 has a cruciform slot 813 for accepting a phillips head screwdriver, as seen in FIG. 15. Screw 810 has a shank 814 having threads 826A, 826B, 826C. Threads 826B form a zone of threads bearing grooves 828 which grooves 828 are similar in configuration to grooves 28 of FIG. 1. Surrounding grooves 826A, 826C lack grooves. Screw 810 optionally has a cylindrical section 817 disposed beneath head 812 and above threads 826A.

The invention is susceptible to variations and modifications which may be introduced without departing from the inventive concept. In one example, a groove may be formed to have a single curved face rather than two or three flat faces as depicted herein. These latter examples would be considered equivalent to the embodiments explicitly shown and described provided that the leading portions of the faces, considered when threading the implant into bone, were arranged at a steeper angle relative to the circumferential outer surface than were the trailing portions.

Also, the angle formed between the leading face (faces 30, 130, 230, 330, and 430 throughout the various described embodiments) may vary from the nearly perpendicular relation to corresponding trailing faces 32, 132, 232, 332, and 432.

Obviously, the invention applies to left handed threading as well as to right handed threading. Furthermore, threads may be configured in a manner shown in my prior U.S. Pat. No. 5,601,429 if desired, rather than featuring threads having equal pitching of upper and lower thread surfaces. In further variations, where it is tapered, the shank of the implant may be curved, stepped, or otherwise configured, rather than frustoconical, as depicted in FIG. 1. Sockets, where they are non-circular, may have recesses configured to be cruciform, star shaped, slotted, or otherwise to cooperate with configuration of conventional driving tools. They may also be irregular if desired.

The invention is equally applicable in the dental field to angled abutments, wherein the socket is not coaxial with the shank. The invention applies equally to other types of medical implants. However, the invention has wider industrial applications as an anchor and even more broadly considered as an industrial fastener. In regard to the latter, conventional fastener heads (not shown), such as hexagonal or other polygonally configured heads, and heads bearing sockets, such as cap screws adapted to receive hexagonal driving keys, square driving keys, star shaped driving keys, and others may be provided in place of recess 20 or other configurations of receptacle 12. The constituent material may be varied from the example of titanium, comprising steel and other metals and alloys, for example.

It is to be understood that the present invention is not limited to the embodiments described above, but encompasses any and all embodiments within the scope of the following claims.

I claim:

1. An implant for securing a prosthesis within live bone tissue, comprising a receptacle having a socket for engaging the prosthesis and a shank for anchoring said receptacle to the bone tissue, wherein said implant includes a proximal end located at said receptacle and a distal end located at said shank, wherein said receptacle is attached to said shank and has structure disposed to cooperate with and attach to the prosthesis, and said shank has an elonqate body having a longitudinal axis, an external circumferential surface, a distal end, threads disposed upon and extending substantially along and outside said external surface said threads having a direction of advance, and at least one groove oriented at a non-parallel angle to and interrupting said threads, wherein at least one of said at least one groove has a first face formed at at least one of said threads interrupted by said at least one of said at least one groove, said first face disposed at a first angle relative to a first line which is tangent to the circumferential surface of the shank at the point of intersection of the first face and said circumferential surface, said first face being exposed in a direction opposite to said direction of advance when said implant is installed into the bone tissue, and a second face formed in the same said thread, said second face being disposed at a second angle relative to a second line which is tangent to the circumferential surface of the shank at the point of intersection of the second face and said circumferential surface, said second face being closer to parallel with said second tangent line than said first face is to being parallel with said first tangent line.

2. The implant according to claim 1, wherein each said groove terminates at a point above said distal end of said dental implant such that an area unencumbered by a said groove exists on said shank between said distal end of said dental implant and every said groove.

3. The implant according to claim 1, wherein at least one said groove interrupts more than half of said threads.

4. The implant according to claim 1, wherein every said groove cuts only into said threads and avoids impinging upon said shank.

5. The implant according to claim 1, wherein said at least one groove is a plurality of grooves and said grooves abut in that a said first face of one said groove abuts a said second face of another said groove.

6. The implant according to claim 1, wherein said at least one groove is a plurality of grooves and said grooves are spaced apart from one another such that said first faces of said grooves are spaced out of abutment with said second faces of said grooves.

7. The implant according to claim 1, wherein a said groove has a third face disposed at a non-parallel angle to said first face and at a non-parallel angle to said second face.

8. The implant according to claim 1, wherein said shank is tapered.

9. The implant according to claim 1, wherein said receptacle has threads.

10. The implant according to claim 1, wherein said receptacle includes a non-cylindrical recess formed therein and opening to said proximal end of said implant, for cooperatively receiving a tool for turning said implant.

11. The implant according to claim 1, wherein said receptacle includes at least one cylindrical recess formed therein and opening to said proximal end of said implant.

12. The implant according to claim 1, wherein said receptacle has a threaded cylindrical recess formed therein and a non-cylindrical recess opening to said proximal end of said implant.

13. The implant according to claim 1, wherein at least one of said faces has some curvature.

14. The implant according to claim 1, wherein the pitch of said thread is at any angle to longitudinal axis of said shank other than perpendicular.

15. The implant according to claim 1, wherein said recess is non-cylindrical and has threads disposed therein.

16. The implant according to claim 1, wherein said at least one groove is a plurality of grooves, and said grooves are spaced apart.

17. An implant for being secured within live bone tissue, comprising a receptacle for engaging an insertion device and a shank for anchoring said receptacle to the bone tissue, wherein said implant includes a proximal end located at said receptacle and a distal end located at said shank, wherein said receptacle is attached to said shank and has a non-cylindrical recess formed therein and opening to said proximal end of said implant, and said shank has an elongate body having a longitudinal axis, an external circumferential surface, a distal end, threads disposed upon and extending substantially along and outside said external surface, said threads having a direction of advance, and at least one groove oriented at a non-parallel angle to said threads and interrupting at least one of said threads, wherein at least one of said at least one groove has a first face formed at at least one of said threads interrupted by said at least one of said at least one groove, said first face disposed at a first angle relative to a line which is tangent to the circumferential surface of the shank at the point of intersection of the first face and said external circumferential surface, said first face being exposed in a direction opposite to said direction of advance when said implant is installed into the bone tissue and a second face formed in the same said thread, said second face being disposed at a second angle relative to a second line which is tangent to the circumferential surface of the shank at the point of intersection of the second face and said circumferential surface, said second face being closer to parallel with said second tangent line than said first face is to being parallel with said first tangent line.

18. The implant according to claim 17, wherein a said groove has at least one additional face disposed at an angle to at least one of the first and second faces of said groove.

19. The implant according to claim 17 wherein a said groove has at least one curved face.

20. The implant according to claim 17, wherein the pitch of said thread is at any angle to said longitudinal axis of said shank other than perpendicular.

21. The implant according to claim 17, wherein said recess is non-cylindrical and has threads disposed therein.

22. The implant according to claim 17, wherein said at least one groove is a plurality of grooves and said grooves are spaced apart.

23. An implant for securing a prosthesis within live bone tissue, comprising a receptacle for engagement and a shank for anchoring said receptacle to the bone tissue, wherein said implant includes a proximal end located at said receptacle and a distal end located at said shank, wherein said receptacle is attached to said shank and has a recess formed therein and opening to said proximal end of said implant, dimensioned and configured to cooperatively receive a tool for driving said implant, and said shank has an elongate body having a longitudinal axis, an external circumferential surface, a distal end, threads disposed upon and extending substantially along and outside said external surface, said threads having a direction of advance, and at least one groove oriented at a non-parallel angle to and interrupting at least one of said threads, wherein at least one of said at least one groove has a first face formed at at least one of said threads interrupted by said at least one of said at least one groove, said first face disposed at a first angle relative to a first line which is tangent to the circumferential surface of the shank at the point of intersection of the first face and said circumferential surface, said first face being exposed in a direction opposite to said direction of advance when said implant is installed into the bone tissue and a second face formed in the same said thread, said second face being disposed at a second angle relative to a second line which is tangent to the circumferential surface of the shank at the point of intersection of the second face and said circumferential surface, said second face being closer to parallel with said second tangent line than said first face is to being parallel with said first tangent line.

24. The implant according to claim 23, wherein at least one of said faces has some curvature.

25. The implant according to claim 23, wherein the pitch of said thread is at any angle to said longitudinal axis of said shank other than perpendicular.

26. The implant according to claim 23, wherein said recess is non-cylindrical and has threads disposed therein.

27. The implant according to claim 23, wherein said at least one groove is a plurality of grooves and said grooves are spaced apart.

28. An implant for securing a prosthesis within live bone tissue, comprising a receptacle for engaging a tool for insertion and a shank for anchoring said implant to the bone tissue, wherein said implant includes a proximal end located at said receptacle and a distal end located at said shank, wherein said receptacle is attached to said shank and has a recess formed therein and opening to said proximal end of said implant said shank has an elongate body having a longitudinal axis, an external circumferential surface, a distal end, threads disposed upon and extending substantially along and outside said external surface, said threads having a direction of advance, and at least one groove oriented at a non-parallel angle to said threads and interrupting at least one of said threads and cutting completely through said at least one thread, and wherein at least one of said at least one groove has a first face formed at least one of said threads interrupted by at least one of said at least one groove, said first face disposed at a first angle relative to a first line which is tangent to the circumferential surface of the shank at a point of intersection of the first face and said circumferential surface, said first face being exposed in a direction opposite to said direction of advance when said implant is installed into the bone tissue, and a second face formed in the sane thread, said second face being disposed at a second angle relative to a second line which is tangent to the circumferential surface of the shank at the point of intersection of the second face and said circumferential surface, said second face being closer to parallel with said second tangent line than said first face is to being parallel with said first tangent line.

29. The implant according to claim 28, wherein the pitch of said thread is at any angle to said longitudinal axis of said shank other than perpendicular.

30. The recess according to claim 28, wherein said recess is non-cylindrical and has threads disposed therein.

* * * * *